(12) United States Patent
Wang et al.

(10) Patent No.: US 9,764,998 B2
(45) Date of Patent: Sep. 19, 2017

(54) PROCESS FOR MAKING HCFO-1233ZD

(71) Applicant: Honeywell International Inc., Morris Plains, NJ (US)

(72) Inventors: Haiyou Wang, Amherst, NY (US); Hsueh Sung Tung, Getzville, NY (US); Stephen A. Cottrell, Baton Rouge, LA (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/088,599

(22) Filed: Apr. 1, 2016

(65) Prior Publication Data

US 2016/0332936 A1 Nov. 17, 2016

Related U.S. Application Data

(60) Provisional application No. 62/160,021, filed on May 12, 2015.

(51) Int. Cl.
*C07C 17/25* (2006.01)
*C07C 21/18* (2006.01)

(52) U.S. Cl.
CPC .................... *C07C 17/25* (2013.01)

(58) Field of Classification Search
CPC ................ C07C 17/25; C07C 21/18
See application file for complete search history.

(56) References Cited

U.S. PATENT DOCUMENTS

| 5,710,352 A | 1/1998 | Tung |
| 8,653,309 B2 * | 2/2014 | Wang ...................... C07C 17/25 570/151 |
| 8,704,017 B2 * | 4/2014 | Pokrovski ............. C01B 7/0706 570/155 |
| 8,835,700 B2 | 9/2014 | Pokrovski et al. |
| 2012/0271069 A1 | 10/2012 | Wang et al. |
| 2012/0271070 A1 | 10/2012 | Wang et al. |
| 2014/0005446 A1 | 1/2014 | Imura et al. |

FOREIGN PATENT DOCUMENTS

WO  2014175403 A1  10/2014

* cited by examiner

*Primary Examiner* — Jafar Parsa
(74) *Attorney, Agent, or Firm* — Bruce O. Bradford

(57) ABSTRACT

Disclosed is a process for the production of 1-chloro-3,3,3-trifluoropropene (HCFO-1233zd) which includes reacting a propane feedstock comprising tetrachlorofluoropropanes, trichlorodifluoropropanes, dichlorotrifluoropropanes, or a mixture thereof, in the presence of a solid catalyst. The process generally comprises the following four steps: (i) providing a propane feedstock comprising trichlorodifluoropropanes and dichlorotrifluoropropanes, (ii) reacting the feedstock in a vapor phase reactor in the presence of HF and in the presence of a solid catalyst under conditions effective to form a product stream comprising HCFO-1233zd and unconverted starting materials, (iii) recovering or removing HCl and HF, and (iv) isolating HCFO-1233zd(E), HCFO-1233zd(Z), or both.

20 Claims, No Drawings

PROCESS FOR MAKING HCFO-1233ZD

CROSS-REFERENCE TO RELATED APPLICATIONS

This application claims domestic priority to copending U.S. Provisional Patent Application Ser. No. 62/160,021, filed May 12, 2015, the disclosure of which is hereby incorporated herein by reference.

FIELD OF THE INVENTION

This invention relates to methods for producing hydrochlorofluoroolefins (HCFOs), particularly trans-1-chloro-3,3,3-trifluoropropene (HCFO-1233zd(E)).

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has two isomers with different physical properties. As one example of the different properties between the two isomers, 1233zd(Z) has a boiling point of approximately 38° C., whereas 1233zd (E) has a boiling point of approximately 19° C. In some applications, it is desirable to use either pure 1233zd(E), pure 1233zd(Z), a particular blend of the (Z) and (E) isomers, or a particular blend of one or both of the 1233zd isomers and another compound in order to control the properties of the solution. For example, in some solvent applications, it is desirable to have a relatively high boiling point. In some such applications, pure 1233zd(Z) may have more desirable physical properties (e.g., a higher boiling point) than either pure 1233zd(E) or mixtures of the two 1233zd isomers.

Processes for synthesizing 1233zd are known. For example, PCT Publication No. WO 97/24307 discloses a process for preparing 1233zd via the gas-phase reaction of 1,1,1,3,3-penta-chloropropane (HCC-240fa) with hydrogen fluoride (HF). However, this process produces relatively low yields of 1233zd.

U.S. Pat. No. 6,844,475 describes a catalytic liquid phase reaction of HCC-240fa with HF to produce 1233zd in higher yields. However the presence of the fluorination catalyst promotes the formation of heavy by-products, oligomers, and tars which can build up in the reactor over time and lead to catalyst dilution and catalyst deactivation, resulting in loss of productivity due to excessive downtime to remove these by-products from the reactor on a periodic basis.

U.S. Pat. No. 8,704,017 discloses a non-catalytic liquid phase reaction of HCC-240fa with HF to reduce the formation of heavy by-products. However, one drawback of not using a catalyst is the problem of slower reaction rates, resulting in the formation of significant amounts of stable underfluorinated intermediates comprising tetrachlorofluoropropanes including 1,1,3,3-tetrachloro-1-fluoropropane (HCFC-241fa), trichlorodifluoropropanes including 1,3,3-trichloro-1,1-difluoropropane (HCFC-242fa) and 1,1,3-trichloro-1,3-difluoropropane (HCFC-242fb) and dichlorotrifluoropropanes including 1,1-dichloro-3,3,3-trifluoropropane (HCFC-243fa) and 1,3-dichloro-1,1,3-trifluoro-propane (HCFC-243fb) can be formed, which significantly decreases the single pass productivity of HCFC-1233zd.

U.S. Pat. No. 9,045,386 describes a process to produce trans-1-chloro-3,3,3-trifluoropropene (HCFO-1233zd(E)) at high purity on a commercial scale. This patent publication is hereby incorporated herein by reference.

Based on the above, there remains a need for means by which partially fluorinated intermediates can be converted into the target product, namely, HCFO-1233zd. This invention satisfies that need.

SUMMARY OF THE INVENTION

The present invention provides methods for the production of 1-chloro-3,3,3-trifluoropropene (HCFO-1233zd). The process generally comprises the following four steps:
(1) providing a feedstock comprising tetrachlorofluoropropanes, trichlorodifluoropropanes and dichlorotrifluoropropanes,
(2) reacting the feedstock in a vapor phase reactor in the presence of HF and in the presence of a solid catalyst under conditions effective to form a product stream comprising HCFO-1233zd, HCl and unconverted starting materials,
(3) recovering or removing HCl and HF, and
(4) isolating HCFO-1233zd(E), HCFO-1233zd(Z), or both.

Non-limiting examples of tetrachlorofluoropropanes include, but are not limited to, 1,1,3,3-tetrachloro-1-fluoropropane (HCFC-241fa). Non-limiting examples of trichlorodifluoropropanes include, but are not limited to, 1,3,3-trichloro-1,1-difluoro-propane (HCFC-242fa) and 1,1,3-trichloro-1,3-difluoropropane (HCFC-242fb). Non-limiting examples of dichlorotrifluoropropanes include, but are not limited to, 1,1-dichloro-3,3,3-trifluoropropane (HCFC-243 fa) and 1,3-dichloro-1,1,3-trifluoropropane (HCFC-243fb). A preferred feedstock comprises a mixture of HCFC-241, HCFC-242 and HCFC-243 (HCFC-242/HCFC-243).

In certain embodiments, the feedstock contains the sum of tetrachlorofluoropropanes, trichlorodifluoro-propanes and dichlorotrifluoropropanes of at least 50 wt %, preferably at least 80 wt %, more preferably at least 90 wt %, and most preferably at least 95 wt %.

In certain embodiments, the solid catalyst may be one or more of halogenated metal oxides in bulk form or supported, metal halides in bulk form or supported, and carbon supported transition metals. Suitable catalysts non-exclusively include halogenated metal oxides (e.g., fluorinated $Cr_2O_3$, fluorinated $Al_2O_3$, fluorinated MgO), metal halides (e.g., $CrF_3$, $AlF_3$, $AlCl_3$, $FeCl_3$, $FeCl_3/C$) and carbon supported transition metals (zero oxidation state) such as Fe/C, Co/C, Ni/C, and Pd/C.

Thus, one embodiment of the invention provides a method for producing a chlorofluoroalkene comprising the following steps:

provided a feedstock comprising tetrachlorofluoropropanes, trichlorodifluoropropanes and dichlorotrifluoropropanes, reacting the feedstock in a vapor phase reactor in the presence of anhydrous HF and in the presence of a solid catalyst under conditions effective to form a product stream comprising HCFO-1233zd, HCl and unconverted starting materials, recovering or removing HCl and HF, and isolating HCFO-1233zd(E), HCFO-1233zd(Z), or both.

Another embodiment of the invention provides a method for producing a chlorofluoroalkene comprising the following steps:

providing a feedstock comprising tetrachlorofluoropropanes, trichlorodifluoropropanes and dichlorotrifluoropropanes, reacting the feedstock in a vapor phase reactor in the presence of a solid catalyst under conditions effective to form a product stream comprising HCFO-1233zd, HCl and unconverted starting materials, recovering or removing HCl and HF, and isolating HCFO-1233zd(E), HCFO-1233zd(Z), or both.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As set forth above, the present invention is directed to a process for producing 1233zd, which comprises:

providing a feedstock comprising tetrachlorofluoropropanes, trichlorodifluoropropanes and dichlorotrifluoropropanes, reacting the feedstock in a vapor phase reactor in the presence of HF and in the presence of a solid catalyst under conditions effective to form a product stream comprising HCFO-1233zd, HCl and unconverted starting materials, and isolating HCFO-1233zd(E), HCFO-1233zd(Z), or both.

In certain embodiments, the feedstock contains the sum of tetrachlorofluoropropanes, trichlorodifluoro-propanes and dichlorotrifluoropropanes of at least 50 wt %, preferably at least 80 wt %, more preferably at least 90 wt %, and most preferably at least 95 wt %. Non-limiting examples of tetrachlorofluoropropanes include, but are not limited to, 1,1,3,3-tetrachloro-1-fluoropropane (HCFC-241fa). Non-limiting examples of trichlorodifluoropropanes include, but are not limited to, 1,3,3-trichloro-1,1-difluoropropane (HCFC-242fa) and 1,1,3-trichloro-1,3-difluoropropane (HCFC-242fb). Non-limiting examples of dichlorotrifluoropropanes include, but are not limited to, 1,1-dichloro-3,3,3-trifluoropropane (HCFC-243fa) and 1,3-dichloro-1,1,3-trifluoropropane (HCFC-243fb).

In preferred embodiments, distillation is used to isolate tetrachlorofluoropropanes, trichlorodifluoropropanes and dichlorotrifluoropropanes from a product stream comprising HCFO-1233zd(E), HCFO-1233zd(Z), HCFC-241fa, HCFC-242fa, HCFC-242fb, HCFC-243fa, and HCFC-243fb. These intermediates can be isolated as individual compounds or as a mixture. As disclosed in U.S. Pat. No. 8,835,700, such a product stream can be obtained by reacting HCC-240fa with anhydrous HF in a liquid phase reactor in the absence of any catalyst. This patent is hereby incorporated herein by reference.

The reaction of tetrachlorofluoropropanes (HCFC-241), trichlorodifluoropropanes (HCFC-242) and dichlorotrifluoropropanes (HCFC-243) may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single pipe or multiple tubes packed with a solid catalyst. Three kinds of catalysts can be used, which include 1) bulk or supported metal halides, 2) bulk or supported halogenated metal oxides, and 3) bulk or supported zero-valent metals. Useful catalysts non-exclusively include fluorinated $Cr_2O_3$, fluorinated $Al_2O_3$, fluorinated MgO, $CrF_3$, $AlF_3$, $AlCl_3$, $FeCl_3$, $MgF_2$, $FeCl_3/C$ and carbon supported transition metals (zero oxidation state) such as Fe/C, Co/C, Ni/C, and Pd/C. The HCFC-242/HCFC-243 feed is introduced into the reactor either in pure form, impure form, or together with an optional inert gas diluent such as nitrogen, argon, or the like.

In some embodiments of the invention, the HCFC-241/HCFC-242/HCFC-243 feedstock is pre-vaporized or pre-heated prior to entering the reactor. Alternatively, the HCFC-241/HCFC-242/HCFC-243 feed is vaporized inside the reactor. Useful reaction temperatures may range from about 200° C. to about 600° C. Preferred temperatures may range from about 250° C. to about 450° C., and more preferred temperatures may range from about 300° C. to about 350° C. The reaction may be conducted at atmospheric pressure, super-atmospheric pressure or under vacuum. The vacuum pressure can be from about 5 Torr to about 760 Torr. Contact time of the HCFC-241/HCFC-242/HCFC-243 feed with the catalyst may range from about 0.5 seconds to about 120 seconds, however, longer or shorter times can be used.

In preferred embodiments, HF is co-fed to the reactor together with the HCFC-241/HCFC-242/HCFC-243 feed. HF is pre-vaporized or preheated prior to entering the reactor. Alternatively, HF is vaporized inside the reactor. The applicants unexpectedly found that the presence of HF co-feed can significantly suppress the formation of some undesirable by-products non-exclusively including dichlorodifluoropropenes (HCFO-1232 isomers), trichlorofluoropropenes (HCFO-1231 isomers), tetrachloropropenes (HCO-1230 isomers), etc. The molar ratio of HF/organic can be ranged from 0.01:1 to 10:1, preferably from 0.1:1 to 5:1, and more preferably from 0.5:1 to 3:1.

In preferred embodiments, the process flow is in either the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 200° C. to about 500° C., preferably from about 300° C. to about 400° C., for from about 0.5 hour to about 3 days. This is followed by H2 treatment at temperatures of from about 100° C. to about 400° C., preferably from about 200° C. to about 300° C. for supported transition metal catalysts or followed by HF treatment at temperatures of from about 200° C. to about 600° C. and preferably from about 300° C. to about 400° C. for halogenated metal oxide catalysts and metal halide catalysts.

The reaction typically yields a reaction product comprising HCFO-1233zd and one or more compounds other than HCFO-1233zd. The reaction product typically takes the form of a mixture of the following: unreacted starting materials, e.g., HCFC-241 isomers, HCFC-242 isomers, and HCFC-243 isomers, and HF in case HF is co-fed; target products, e.g., HCFO-1233zd; and by-products, e.g., HCl, HF, HFO-1234ze, HFC-245fa, HCFC-244fa, HCFO-1232 isomers, HCFO-1231 isomers, HCO-1230 isomers, etc.

Desirable levels of raw material conversion and HCFO-1233zd selectivity can be impacted by operating parameters, including conditions such as reaction temperature, pressure, and residence time. The reaction will be carried out at conditions sufficient to effect the formation of target product. Selectivity to HCFC-1233zd (the sum of two isomers) with the preferred catalysts is about 50% or more, more preferably about 70 or more, and most preferably about 90% or more. Conversion of raw material is preferably about 10% or more, more preferably about 40% or more, and most preferably about 70% or more.

HCFC-1233zd may be recovered from the reaction product as either or both of E and Z-isomers thereof. Recovery of compounds from the reaction product may be affected by any means known in the art, such as by extraction and preferably by distillation. For example, the distillation may be conducted in a standard distillation column at a pressure less than about 300 psig, preferably less than about 150 psig, and most preferably less than 100 psig. The pressure of distillation column inherently determines the distillation operating temperature. HCl may be recovered by operating the distillation column at from about −40° C. to about 25° C., preferably from about −40° C. to about −20° C. HCFO-1233zd may be recovered by operating the distillation column at from about −10° C. to about 60° C. Single or multiple distillation columns may be used. If, desired, the HCFO-1233zd(E) and HCFO-1233zd(Z) may be separated from each other by means known in the art, such as extraction and distillation.

In a preferred embodiment, HCl is removed from the reaction products. More preferably, the HCl is removed prior to the recovery of HCFC-1233zd from the reaction product mixture. The HCl in the product stream is recovered using an HCl column. High purity HCl is isolated from the top of the column and absorbed in de-ionized water as concentrated HCl. Alternatively, HCl can be recovered or removed from the product stream by using water or caustic scrubbers. When water extractor is used, HCl aqueous solution of various concentrations is formed. When caustic scrubber is used, HCl is neutralized as a chloride salt in aqueous solution.

In certain embodiments, the essentially HCl-free organic/HF mixture is fed to a sulfuric extractor or a phase separator for removal of HF from this mixture. HF is either dissolved in the sulfuric acid or phase separated from the organic mixture. For embodiments utilizing a sulfuric acid adsorption system, sulfuric acid is preferably added such that the weight ratio of sulfuric acid to hydrogen fluoride ranges from about 1:1 to about 10:1. More preferably the weight ratio ranges from about 1:1 to about 8:1 and most preferably from about 2:1 to about 4:1. The HF is then desorbed from the sulfuric acid/HF mixture by stripping distillation and recycled back to the fluorination reactor. For embodiments utilizing a phase separator, preferably the extraction is conducted at a temperature of from about −20° C. to about 100° C., more preferably from about −10° C. to about 60° C., and most preferably from about 0° C. to about 40° C. The HF is then phase-separated and recycled back to the reactor. The organic mixture either from the overhead of the sulfuric acid extractor or from the bottom layer of the phase separator may require treatment (scrubbing or adsorption) to remove traces of HF before it is sent to next unit operation for product isolation.

In certain embodiments, the isomers HCFO-1233zd(E) and HCFO-1233zd(Z) are isolated as two products. Acid free crude product is first sent to a distillation column, from which HCFO-1233zd(E) exits the top of the column together with some light components having lower boiling points than HCFO-1233zd(E) while HCFO-1233zd(Z) exits from the bottom of the column together with some heavy components having higher boiling points than HCFO-1233zd(Z). The overhead stream and the bottom stream are then sent to two separate columns for further purification to obtain HCFO-1233zd(E) and HCFO-1233 zd(Z) products.

EXAMPLES

The following examples are provided to further illustrate the invention and should not be taken as limitations of the invention.

Example 1

In this example, 5 wt % $FeCl_3$/carbon was used as a catalyst. A ¾ inch×0.035 inch tube Inconel 625 reactor was used. The reactor was installed in the middle of an electric 3-zone split furnace. Process temperatures were recorded using a multi-point thermocouple placed inside the reactor and within the catalyst bed. The distance between two adjacent probe points was 4 inches. 40 ml of solid catalyst was loaded in such a way that its bed was within three adjacent probe points. The reactor was heated to desired temperatures in nitrogen flow and 51.6 GC area % 243 (two isomers with 243fb being dominant component)/47.5 GC area % 242fa feed was then fed into the bottom of the vertically mounted reactor to start a reaction. The reaction effluent was periodically sampled for its compositions.

As shown in Table 1, the percentages of 1233zd (1233zdE plus 1233zdZ) in vapor phase and in liquid phase were about 33%, and about 2.5%, respectively.

TABLE 1

| GC-MS analysis of product generated over 5 wt % FeCl3/carbon catalyst at 200° C.* | | | | |
|---|---|---|---|---|
| Peak | Retention Time | | FID area % | |
| No. | (min) | Species | Vapor phase | Liquid phase |
| 1 | 10.078 | G-13 | 0.389 | — |
| 2 | 10.328 | Difluoroethene | 0.397 | — |
| 3 | 14.982 | G-245fa | 0.439 | — |
| 4 | 15.742 | Chlorofluoroethene | 1.004 | — |
| 5 | 17.338 | chloroethene | 0.305 | — |
| 6 | 19.435 | G-1233zdE | 30.139 | 2.192 |
| 7 | 20.368 | G-244fa | 0.675 | 0.122 |
| 8 | 21.348 | G-1233zdZ | 2.944 | 0.455 |
| 9 | 21.810 | C6H4F8 isomer | — | 0.224 |

TABLE 1-continued

GC-MS analysis of product generated over
5 wt % FeCl3/carbon catalyst at 200° C.*

| Peak No. | Retention Time (min) | Species | FID area % Vapor phase | FID area % Liquid phase |
|---|---|---|---|---|
| 10 | 21.954 | dichloroethene | 0.441 | 0.060 |
| 11 | 23.272 | G-1232 isomer | 0.953 | 0.397 |
| 12 | 23.397 | 243 isomer | 12.325 | 10.060 |
| 13 | 23.628 | 243 isomer | 40.971 | 40.988 |
| 14 | 24.301 | G-1233zd dimer | — | 0.222 |
| 15 | 25.878 | G-242 isomer | 7.776 | 44.674 |
| 16 | 27.080 | G-1110 | — | 0.058 |
| 17 | 28.590 | G-1230 isomer | — | 0.481 |

*Other reaction conditions: 40 ml of 5 wt % FeCl3/carbon catalyst, 0 psig, 15 g org/h, 51.6 GC area %243 (two isomers with 243fb being dominant component)/47.5 GC area %242fa Example 2

In this example, fluorinated $Cr_2O_3$ was used as a catalyst. A ¾ inch×0.035 inch tube Inconel 625 reactor was used. The reactor was installed in the middle of an electric 3-zone split furnace. Process temperatures were recorded using a multi-point thermocouple placed inside the reactor and within the catalyst bed. The distance between two adjacent probe points was 4 inches. 20 ml of solid catalyst was loaded in such a way that its bed was within two adjacent probe points. The reactor was heated to desired temperatures in nitrogen flow and 51.6 GC area % 243 (two isomers with 243fb being dominant component)/47.5 GC area % 242fa feed was then fed into the bottom of the vertically mounted reactor to start a reaction. The reaction effluent was periodically sampled for its compositions. As shown in Table 2, the percentages of 1233zd (1233zdE plus 1233zdZ) in vapor phase and in liquid phase were about 81%, and about 35%, respectively.

TABLE 2

GC-MS analysis of product generated over
fluorinated $Cr_2O_3$ catalyst at 250° C.*

| Peak No. | Retention Time (min) | Species | FID area % Vapor phase | FID area % Liquid phase |
|---|---|---|---|---|
| 1 | 10.049 | G-23 | 0.151 | — |
| 2 | 10.799 | G-142 isomer | 0.680 | — |
| 3 | 13.021 | G-1234 isomer | 0.444 | — |
| 4 | 14.261 | G-12 | 0.151 | — |
| 5 | 15.021 | G-245fa | 0.199 | — |
| 6 | 17.358 | chloroethene | 0.521 | 0.065 |
| 7 | 19.637 | G-1233zdE | 72.524 | 30.139 |
| 8 | 19.887 | G-1335 isomer | 0.137 | 0.062 |
| 9 | 20.425 | G-244fa | 1.403 | 0.853 |
| 10 | 21.426 | G-1233zdZ | 8.410 | 4.683 |
| 11 | 21.791 | C6H4F8 isomer | — | 0.127 |
| 12 | 22.012 | dichloroethene | 1.117 | 0.576 |
| 13 | 22.82 | 1223xd | 0.372 | 0.410 |
| 14 | 23.32 | G-1232 isomer | 2.966 | 4.340 |
| 15 | 23.445 | 243 isomer | 3.650 | 8.474 |
| 16 | 23.618 | 243 isomer | 4.999 | 13.418 |
| 17 | 24.051 | G-1232 isomer | — | 0.150 |
| 18 | 24.291 | G-1233zd dimer | — | 0.328 |
| 19 | 24.368 | G-1232 isomer | 0.167 | 0.471 |
| 20 | 25.811 | G-242 isomer | 1.776 | 25.128 |
| 21 | 26.445 | G-1231 isomer | — | 0.408 |
| 22 | 26.436 | G-1231 isomer | — | 0.492 |
| 23 | 26.686 | unknown | — | 0.718 |
| 24 | 28.599 | G-1230 isomer | 0.154 | 17.813 |
| 25 | 33.081 | unknown | — | 0.301 |

*Other reaction conditions: 20 ml of spent chromia catalyst, 0 psig, 15 g org/h, 51.6 GC area %243 (two isomers with 243fb being dominant component)/47.5 GC area %242fa Example 3

In this example, the same fluorinated $Cr_2O_3$ catalyst was used as in Example 2. A ¾ inch×0.035 inch tube Inconel 625 reactor was used. The reactor was installed in the middle of an electric 3-zone split furnace. Process temperatures were recorded using a multi-point thermocouple placed inside the reactor and within the catalyst bed. The distance between two adjacent probe points was 4 inches. 20 ml of solid catalyst was loaded in such a way that its bed was within two adjacent probe points. The reactor was heated to desired temperatures in nitrogen flow and 51.6 GC area % 243 (two isomers with 243fb being dominant component)/47.5 GC area % 242fa feed and anhydrous HF were then fed into the bottom of the vertically mounted reactor to start a reaction. The reaction effluent was periodically sampled for its compositions. Applicants unexpectedly found by co-feeding the amount of 1230 isomer generated was greatly reduced to below 1% (versus about 18% in the absence of HF) while the amount of 1233zd remained about the same.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the production of 1-chloro-3,3,3-trifluoropropene (HCFO-1233zd) which comprises the steps of:
   (i) providing only a partially fluorinated propane feedstock selected from the group consisting of tetrachlorofluoropropanes, trichlorodifluoropropanes, dichlorotrifluoro-propanes, and mixtures thereof;
   (ii) reacting the propane feedstock in a vapor phase reactor in the presence of HF and in the presence of a solid catalyst under conditions effective to form a product stream comprising HCFO-1233zd isomers, HCl and unconverted starting materials,
   (iii) recovering or removing HCl and HF, and
   (iv) isolating the HCFO-1233zd E-isomer, the HCFO-1233zd Z-isomer, or both compounds.

2. The process of claim 1, wherein the propane in the feedstock comprises 1,1,3,3-tetrachloro-1-fluoropropane (HCFC-241fa).

3. The process of claim 1, wherein the propane in the feedstock comprises 1,3,3-trichloro-1,1-difluoro-propane (HCFC-242fa).

4. The process of claim 1, wherein the propane in the feedstock comprises 1,1,3-trichloro-1,3-difluoropropane (HCFC-242fb).

5. The process of claim 1, wherein the propane in the feedstock comprises 1,1-dichloro-3,3,3-trifluoropropane (HCFC-243fa).

6. The process of claim 1, wherein the propane in the feedstock comprises, 1,3-dichloro-1,1,3-trifluoropropane (HCFC-243fb).

7. The process of claim 1, wherein the solid catalyst comprises one or more halogenated metal oxides in bulk form or supported, metal halides in bulk form or supported, and carbon supported transition metals.

8. The process of claim 7, wherein the catalyst comprises one or more halogenated metal oxides selected from the group consisting of fluorinated $Cr_2O_3$, fluorinated $Al_2O_3$, and fluorinated MgO.

9. The process of claim 7, wherein the catalyst comprises one or more metal halides selected from the group consisting of $CrF_3$, $AlF_3$, $AlCl_3$, $FeCl_3$, and $FeCl_3/C$.

10. The process of claim 7, wherein the catalyst comprises one or more carbon supported zero oxidation state transition metals selected from the group consisting of Fe/C, Co/C, Ni/C, and Pd/C.

11. The process of claim 1, wherein the feedstock comprises a mixture of HCFC-241, HCFC-242 and HCFC-243, which is introduced into the reactor either in pure form, impure form, or together with an optional inert gas diluent.

12. The process of claim 11, wherein the HCFC-241, HCFC-242 and HCFC-243 feedstock is pre-vaporized or preheated prior to entering the reactor.

13. The process of claim 11, wherein the HCFC-241, HCFC-242 and HCFC-243 feedstock is vaporized inside the reactor.

14. The process of claim 11, wherein the reactor temperature ranges from about 200° C. to about 600° C.

15. The process of claim 11, wherein the reaction pressure is selected from the group consisting of atmospheric pressure, super-atmospheric pressure and under vacuum, wherein the vacuum pressure can be from about 5 Torr to about 760 Torr.

16. The process of claim 11, wherein the reaction contact time of the HCFC-241, HCFC-242 and HCFC-243 feedstock with the catalyst ranges from about 0.5 seconds to about 120 seconds.

17. The process of claim 11, wherein the HF is co-fed to the reactor together with the HCFC-241, HCFC-242 and HCFC-243 feedstock.

18. The process of claim 17, wherein the HF is pre-vaporized or preheated prior to entering the reactor.

19. The process of claim 17, wherein the HF is vaporized inside the reactor.

20. The process of claim 17, wherein the molar ratio of HF to the HCFC-242 and HCFC-243 feedstock ranges from 0.01:1 to 10:1.

* * * * *